(12) United States Patent
Graham et al.

(10) Patent No.: US 12,364,996 B2
(45) Date of Patent: Jul. 22, 2025

(54) SET CONSISTING OF A PUMP DISPENSER AND AN EVALUATION UNIT

(71) Applicant: Aptar Radolfzell GmbH, Radolfzell (DE)

(72) Inventors: Dominic Alexander Graham, Abingdon (GB); Matthew Meredith Jones, Warwick (GB); Joachim Körner, Uhldingen-Mühlhofen (DE); William Goeffrey Arthur Marsh, Wolverton (GB)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 18/451,310

(22) Filed: Aug. 17, 2023

(65) Prior Publication Data

US 2023/0390795 A1 Dec. 7, 2023

Related U.S. Application Data

(62) Division of application No. 17/281,041, filed as application No. PCT/EP2019/075749 on Sep. 24, 2019, now Pat. No. 11,766,688.

(30) Foreign Application Priority Data

Oct. 8, 2018 (EP) .................................. 18199176

(51) Int. Cl.
- *B05B 12/00* (2018.01)
- *B05B 11/10* (2023.01)
- *G16H 20/13* (2018.01)

(52) U.S. Cl.
CPC ........ *B05B 12/004* (2013.01); *B05B 11/1035* (2023.01); *B05B 11/1047* (2023.01);
(Continued)

(58) Field of Classification Search
CPC ............... B05B 12/004; B05B 11/3035; B05B 11/3047; B05B 11/3069; B05B 11/108; G16H 20/13
See application file for complete search history.

(56) References Cited

U.S. PATENT DOCUMENTS

| | | | | |
|---|---|---|---|---|
| 4,034,757 A | * | 7/1977 | Glover | ....................... A61J 1/00 604/404 |
| 4,565,302 A | * | 1/1986 | Pfeiffer | .................... G01F 15/00 235/117 A |

(Continued)

FOREIGN PATENT DOCUMENTS

| | | |
|---|---|---|
| EP | 2177141 A2 | 4/2010 |
| EP | 3895809 A1 | 10/2021 |

(Continued)

OTHER PUBLICATIONS

International Search Report, with English translation, issued in corresponding International Application No. PCT/EP2019/075749, date of mailing Nov. 20, 2019 (5 pages).

(Continued)

*Primary Examiner* — David P Angwin
*Assistant Examiner* — Randall A Gruby
(74) *Attorney, Agent, or Firm* — FLYNN THIEL, P.C.

(57) ABSTRACT

A set including a pump dispenser for discharging pharmaceutical or cosmetic liquids and an external evaluation unit, which is designed to be exchangeable so that, after the pump dispenser has been emptied, the evaluation unit can be attached to a new pump dispenser. The evaluation unit can be attached to the discharging head of the pump dispenser such that the evaluation unit detects an actuation button and can be partially displaced with same. The evaluation unit can alternatively have a receiving container which is open on at least one side and into which the pump dispenser can be (Continued)

inserted and the force application of which is detected on actuation.

20 Claims, 8 Drawing Sheets

(52) U.S. Cl.
CPC ......... *B05B 11/1069* (2023.01); *G16H 20/13* (2018.01); *B05B 11/108* (2023.01)

(56) References Cited

U.S. PATENT DOCUMENTS

| | | | |
|---|---|---|---|
| 5,020,527 A * | 6/1991 | Dessertine | A61M 15/0065 128/200.14 |
| 5,505,192 A | 4/1996 | Samiotes et al. | |
| 5,544,647 A | 8/1996 | Jewett et al. | |
| 5,564,414 A | 10/1996 | Walker et al. | |
| 5,692,492 A * | 12/1997 | Bruna | A61M 15/0081 128/200.14 |
| 5,772,074 A * | 6/1998 | Dial | G01F 13/006 222/37 |
| 6,202,642 B1 * | 3/2001 | McKinnon | A61M 15/0083 128/200.14 |
| 6,234,366 B1 | 5/2001 | Fuchs | |
| 6,375,038 B1 * | 4/2002 | Daansen | G09B 19/0076 222/638 |
| 6,404,837 B1 * | 6/2002 | Thompson | A47K 5/1217 377/16 |
| D471,120 S * | 3/2003 | Spitz | D10/97 |
| D471,831 S * | 3/2003 | Tomaka | D10/97 |
| 6,595,389 B2 * | 7/2003 | Fuchs | A61M 15/008 222/38 |
| 6,651,844 B2 | 11/2003 | Tomaka et al. | |
| 7,314,187 B2 * | 1/2008 | Hochrainer | B05B 11/108 239/583 |
| 7,315,245 B2 * | 1/2008 | Lynn | G09B 19/0076 340/573.1 |
| 7,477,148 B2 * | 1/2009 | Lynn | A47K 5/1202 340/573.1 |
| 7,661,423 B2 | 2/2010 | Brand et al. | |
| 7,782,214 B1 * | 8/2010 | Lynn | A47K 5/1217 340/572.1 |
| 7,806,295 B2 * | 10/2010 | Stradella | G06M 1/083 222/36 |
| 7,849,851 B2 | 12/2010 | Zierenberg et al. | |
| 8,109,414 B2 * | 2/2012 | Cater | A61M 15/08 222/321.9 |
| 8,141,550 B2 * | 3/2012 | Lawrence | G09F 11/04 128/200.14 |
| 8,169,327 B2 * | 5/2012 | Lynn | A47K 5/1217 340/572.1 |
| 8,528,790 B2 * | 9/2013 | Wegelin | G07C 3/04 222/113 |
| 8,672,187 B2 * | 3/2014 | Ophardt | A47K 5/1217 222/145.5 |
| 8,997,735 B2 | 4/2015 | Zierenberg et al. | |
| 9,131,811 B2 * | 9/2015 | Wegelin | A47K 5/1217 |
| 9,192,954 B2 * | 11/2015 | Kohnle | H02K 7/1853 |
| 9,827,384 B2 * | 11/2017 | Holakovsky | A61M 15/0036 |
| 9,920,553 B2 * | 3/2018 | Limbert | E05B 65/06 |
| 10,065,006 B2 | 9/2018 | Helmlinger | |
| 10,406,304 B2 * | 9/2019 | Koerner | H10N 30/50 |
| 11,207,474 B2 * | 12/2021 | Dunne | B05B 11/0054 |
| 11,369,761 B2 * | 6/2022 | Tritschler | G08B 21/24 |
| 2006/0231568 A1 | 10/2006 | Lynn et al. | |
| 2007/0272764 A1 * | 11/2007 | Poulard | A61M 15/0065 239/71 |
| 2008/0185395 A1 * | 8/2008 | Sahud | A47K 5/1217 222/38 |
| 2009/0266842 A1 * | 10/2009 | Snodgrass | A47K 5/1217 222/326 |
| 2010/0094581 A1 * | 4/2010 | Cagle | B05B 11/108 702/176 |
| 2010/0308076 A1 * | 12/2010 | Snodgrass | B65D 83/262 222/1 |
| 2012/0111446 A1 * | 5/2012 | Butler | B65D 83/7575 141/2 |
| 2012/0234867 A1 * | 9/2012 | Ophardt | A47K 5/1217 429/400 |
| 2013/0098941 A1 | 4/2013 | Wegelin | |
| 2013/0099900 A1 | 4/2013 | Pulvermacher | |
| 2013/0269685 A1 * | 10/2013 | Wachtel | A61M 15/0065 128/200.14 |
| 2014/0131388 A1 | 5/2014 | Heisel et al. | |
| 2015/0235549 A1 * | 8/2015 | Limbert | A47K 5/1217 222/173 |
| 2019/0246848 A1 * | 8/2019 | Elfstrom | H01H 13/18 |
| 2022/0273891 A1 * | 9/2022 | Helmlinger | G16H 20/10 |
| 2023/0129079 A1 | 4/2023 | Karge et al. | |

FOREIGN PATENT DOCUMENTS

| | | | | |
|---|---|---|---|---|
| JP | 2007210680 A | 8/2007 | | |
| JP | 2014530712 A | 11/2014 | | |
| JP | 2014530747 A | 11/2014 | | |
| WO | 9526769 A1 | 10/1995 | | |
| WO | 2005080001 A1 | 9/2005 | | |
| WO | WO-2012096377 A1 * | 7/2012 | ......... | B05B 11/3056 |

OTHER PUBLICATIONS

Written Opinion of International Searching Authority, issued in corresponding International Application No. PCT/EP2019/075749, date of mailing Nov. 20, 2019 (7 pages).
Notice of Reasons for Rejection with English translation issued in corresponding Japanese Application No. 2021-540928 dated Jul. 29, 2022 (8 pages).
Jut Definition and Meaning; Merriam-Webster; obtained on Dec. 8, 2022; http://www.merriam-webster.com/dictionary/jut (13 pages).
Protrude Definition and Meaning; Merriam-Webster; obtained on Dec. 9, 2022; http://www.merriam-webster.com/dictionary/protrude (13 pages).

* cited by examiner

SET CONSISTING OF A PUMP DISPENSER AND AN EVALUATION UNIT

CROSS REFERENCE TO RELATED APPLICATIONS

This is a divisional of U.S. patent application Ser. No. 17/281,041, filed Mar. 29, 2021, which was the National Stage of International Application No. PCT/EP2019/075749, filed Sep. 24, 2019, which claims priority to European Application No. 18199176.1, filed Oct. 8, 2018, the entire contents of which are hereby incorporated by reference.

FIELD OF APPLICATION AND PRIOR ART

The invention relates to a set including a pump dispenser for the discharge of pharmaceutical or cosmetic liquids, and further including an evaluation unit.

Here, in the context of the invention, pump dispensers which are well known from the prior art include a liquid reservoir, at the upper end of which a discharge head is provided. Said discharge head has a base which is fastened to the liquid reservoir, and an actuating button which can be pressed down with respect to the base for the purpose of the discharge. The discharge head has a pump device which can be actuated by way of pressing down of the actuating button, and which, in the case of actuation, conveys liquid from an inlet channel connected to the liquid reservoir, to a discharge opening provided on the discharge head.

Pump dispensers of the described type are comparatively simple apparatuses which can be produced inexpensively. There is the desire for the use of pump dispensers of this type to be logged, in order to provide added benefits both for the user and for the producer of pump dispensers and/or the liquids which are contained therein. The electronic components for the detection and further processing of actuation operations of the pump dispenser are comparatively expensive, however, with the result that the integration into pump dispensers would not as a rule be economical.

Problem and Solution

The invention pertains to a pump dispenser of the above-described type which was developed in such a way that a discharge is detected, in order for it to be possible for the discharge to be processed further using data technology.

For this purpose, it is proposed to provide a set including a pump dispenser of the type mentioned at the outset and an evaluation unit, the evaluation unit being configured for the detection of the actuation of the pump device.

It is the basic concept of the present invention here that the pump dispenser is supplemented by an evaluation unit which is configured as an external evaluation unit. Within the context of the invention, an external evaluation unit is understood to mean that it is not relevant for the basic functionality of the pump dispenser. In the case of a removed evaluation unit, the pump dispenser is functionally capable in a separate state and can be used in a customary way. The external evaluation unit of the set according to the invention supplements said pump dispenser, and can be attached to the outer side of the pump dispenser in such a way that it can detect an actuation by pressing down the actuating button. The evaluation unit is attached to the pump dispenser in a releasable way, with the result that it is easy for the user to replace the pump dispenser and to continue to use the evaluation unit with a new pump dispenser.

A detection sensor which is described in greater detail in the following text is provided for the detection of the actuation of the pump dispenser by pressing down the actuating button. Said detection sensor generates a digital or analog electric signal which can be further processed and/or forwarded by further electronic components of the evaluation unit. The detection sensor is preferably configured as a displacement or force or pressure sensor.

In the case of the evaluation unit being attached to the pump dispenser, said sensor is preferably arranged in the force flow. In the case of customary actuation, said force flow runs from that finger of the user which actuates the actuating button to the actuating button, from there to the base of the discharge head and the liquid reservoir as far as the hand of the user which grips around the liquid reservoir in the case of customary operation.

The detection sensor is preferably arranged in such a way that it detects the movement between the actuating button and the base of the discharge head, or that it detects the force or the pressure between the liquid reservoir and the clasping hand of the user.

Two specific overall designs are proposed, in particular:

In the case of the first overall design, the evaluation unit is configured as an external evaluation unit which has a main segment which is attached releasably in a stationary manner to the liquid reservoir or the base of the discharge head, and which has an actuating segment which can be moved with respect to the main segment and the movement of which with respect to the main segment can be detected by way of the detection sensor, the actuating segment being arranged on or above the actuating button in such a way that, when the actuating button is pressed down with respect to the base, the actuating segment is also moved with respect to the main segment.

In the case of a second overall design, the evaluation unit is configured as an external evaluation unit which has a receiving container which is open at least on one side and into which at least the liquid reservoir is pushed releasably, with the result that at least the discharge opening is disposed outside of the receiving container at a first upper end, the detection sensor being arranged at an opposite second end of the receiving container or at a closure which is attached thereto. The detection sensor, when the actuating button is pressed down, receives a force applied thereto by the liquid reservoir, with the result that the actuation can be detected by the detection sensor.

Depending on the overall design, the detection sensor is preferably of different configurations. In the case of the first overall design, in particular, the detection sensor is a force sensor or displacement sensor, a digital evaluation being sufficient for most applications, with the result that a sensor of this type can be configured, in particular, as a simple switch which detects the movement of the actuating segment with respect to the main segment.

In the case of the second overall design, the detection sensor is preferably a pressure sensor or a force sensor which measures the force applied by the liquid reservoir to the detection sensor.

Other types of sensors can fundamentally also be used as detection sensor, however. Thus, for example, a vibration or acceleration sensor can be used as detection sensor which detects the actuation indirectly, for example by vibrations being sensed which are caused by way of the actuating button passing one or more latching edges. Moreover, the presence of a vibration or acceleration sensor in the evaluation unit is also advantageous for other functions. Thus, for example, it can be determined in this way whether the pump dispenser has been shaken sufficiently before use.

The evaluation unit can also have at least one sensor which is provided for the detection of the liquid quantity which remains in the liquid reservoir. Depending on the configuration, in the case of the second overall design mentioned above, said pressure sensor can also detect in the rest state of the set how heavy the pump dispenser still is and can extrapolate the remaining liquid quantity herefrom.

Moreover, a wide variety of further sensors are conceivable which can expediently be part of the evaluation unit. A sensor system can thus be provided, in order to detect whether the evaluation unit is attached to the pump dispenser. It is also conceivable that an identification label which is unique to the pump dispenser or an identification label which is specific to the liquid in the pump dispenser is read out by the pump dispenser, for example for RFID technology. Further possible sensors are sensors for the detection of the liquid temperature and/or the ambient temperature.

The evaluation unit can be configured in such a way that the detected data are stored directly in it and/or are shown via an indicator apparatus, in particular in the form of light emitting diodes or a display. As an alternative or in addition, it is preferred if the evaluation unit has a wireless data interface, in particular in the manner of a Bluetooth interface, a 4G interface or a 5G interface, via which detected data are transmitted to a server or a separate evaluation device such as a mobile telephone.

The use of a set according to the invention allows pump dispensers which are known per se to be supplemented in a simple way, such that the handling by the user can be detected and processed further. This results in various use possibilities as discussed below.

From the perspective of the user and, in particular, in the region of cosmetic applications, the possibility of data evaluation is advantageous, since the user knows his/her type of usage himself/herself and can receive suggestions in this regard from an evaluating program. A program of this type which runs, in particular, on said external evaluation unit can, for instance, analyze the frequency of use, the specific type of use such as, for example, the type of pressing and the like, and can make suggestions for other supplementary products such as, in particular, cosmetic products. If, in particular, a plurality of dispensers which are used by the user have evaluation units of the above-described type or another type, suggestions can be made in a targeted manner. The evaluation unit can also check the filling level of a dispenser indirectly or directly, and can bring about reordering operations of the corresponding product in an automatic or semi-automatic manner.

In the field of pharmaceutical liquids, a check can be made that application times which are stipulated by a doctor are being observed. The data can optionally be forwarded to the doctor, with the result that he/she gains an overview about the observance of the application times.

Valuable data in respect of typical use can be derived for use by the producer of the liquid stored in the pump dispenser. It can thus be detected whether the frequency of use changes or where the use of the pump dispenser usually takes place.

Said pump dispenser is a substantially customary pump dispenser. There are no necessary adaptations which stand in the way of the use of known pump dispensers with the described evaluation unit. This facilitates the market introduction of the described system. Only if special functionalities are desired, such as, for example, the unique identification of a pump dispenser, in particular via an RFID tag, is there a requirement for an adaptation of the pump dispenser.

Typical measures which are known per se, and which a pump dispenser for use in a set according to the invention has, are the following: the liquid reservoir of the pump dispenser can be connected via a snap-action connection or a threaded connection to the discharge head. As an alternative, the base of the discharge head can be configured in one piece with the liquid reservoir. The liquid reservoir is preferably an elongate body, the main direction of extent of which preferably coincides, in particular, with the movement direction of the actuating button with respect to the base. The liquid reservoir is preferably of substantially circular-cylindrical form, said liquid reservoir usually being provided at an upper end with a latching edge or a thread for coupling the discharge head. In the state in which it is ready for sale, the liquid reservoir is filled with a liquid, preferably with a cosmetic or pharmaceutical liquid, in particular with a cream, an ointment or a lotion.

A pump dispenser which is part of a set according to the invention can have an inscription on its outer side, for example trademarks, indications of contents of the liquid, or instructions for use.

The pump dispenser generically has a pump device, that is to say a device which, when the actuating button is pressed down, isolates a partial quantity of the liquid (located in the liquid reservoir) from the liquid reservoir and subsequently conducts it to the discharge opening, the positive pressure which is provided for the discharge in the pump chamber preferably being generated directly by way of the force applied to the actuating button. In particular, the pump device can have a pump chamber, an inlet-side inlet valve and an outlet-side outlet valve, the inlet valve opening in the case of negative pressure in the pump chamber with respect to the liquid reservoir, and the outlet valve opening in the case of positive pressure in the pump chamber with respect to the surrounding atmosphere. The pump chamber is variable in terms of volume, this preferably being achieved, in particular, by way of a compressible bellows or by way of a pump cylinder with an inner and movable pump piston.

Although designs are possible in which the discharge opening is provided at the base of the discharge head, the design which is more customary in the case of pump dispensers with a discharge opening on the actuating button is preferred in the present case. In the case of a design of this type, when the actuating button is pressed down with respect to the base of the discharge head, the discharge opening is likewise pressed down.

In the case of the first overall design of the evaluation unit, the functional principle is based on the fact that pressing down of the actuating button at the same time causes pressing down of the actuating segment with respect to the main segment which is stationary with respect to the liquid reservoir, which is utilized for the purpose of evaluation. For this purpose, the actuating segment can be attached laterally to the actuating button, with the result that said actuating button continues to be pressed down directly by the user. It is preferred, however, that the actuating segment is arranged between the finger of the user and the actuating button in the case of the actuation, with the result that a force is applied to the actuating button indirectly.

In the case of the second overall design of the evaluation unit, the functional principle is based on the fact that the user does not grip the liquid reservoir directly by way of his/her hand, but rather instead grips the receiving container, on which the liquid reservoir is supported in the case of actuation. Therefore, an action of force which is detected occurs between the liquid reservoir on one side and the receiving container or its closure on the other side.

A set with the first overall design of the evaluation unit preferably comprises a protective cap which, in the fitted state, covers the actuating button and/or the discharge opening. A protective cap of this type is usually supplied together with known pump dispensers. This cap prevents, for example, in the case of transport in a pocket, the actuating button from being accidentally pressed down.

If a protective cap of this type is sufficiently large, it can be possible in individual cases for the evaluation unit of said first overall design to be accommodated completely within the receiving space of the protective cap.

It is preferred, however, that the protective cap is adapted to the discharge head and the main segment of the evaluation unit in such a way that it can be coupled in a non-positive or positively locking manner to the discharge head on one side and to the main segment on the other side. This allows a protective cap to selectively be attached directly to the discharge head or to the liquid reservoir in the case of non-use of the evaluation unit, and to instead attach the protective cap to the evaluation unit in the case of the latter being used. In order to avoid dropping of the protective cap, the latter firstly and the discharge head and the main segment secondly, should be suitable for permitting a stable coupling. This can be achieved, for example, by way of corresponding latching elements, by way of a bayonet or by way of a thread.

The protective cap and the main segment of the evaluation unit can have identical coupling devices which can be coupled in each case to a coupling device on the discharge head or the liquid reservoir. The use of identical coupling devices on the protective cap and on the main segment allows the main segment to be attached on the discharge head or on the liquid reservoir where the protective cap is attached in the case of a missing evaluation unit. The discharge head or the liquid reservoir therefore do not have to be configured in a special way, in order to permit an attachment of the evaluation unit. Nevertheless, minor variations in the dimensions can achieve a situation where an evaluation unit which is coupled on the discharge head or the liquid reservoir can be released only with an increased effort which is higher than the effort which is usually required for the removal of the protective cap.

The main segment of an evaluation unit of the first overall design preferably has a ring section which surrounds a free region, through which the pump dispenser can be pushed as far as into a coupling position. The configuration of the evaluation unit with a ring section is firstly intuitive, since it can be seen very simply through the free region of the ring section how the evaluation unit is to be attached to the pump dispenser. In addition, the ring section permits a particularly stable hold and can also be integrated esthetically in a very satisfactory manner into a commercially available pump dispenser.

The ring section is preferably closed. Designs are also conceivable, however, in the case of which the ring is slotted, for example in order to be widened slightly in the assembled state and, as a result, to make fixing by means of a strong clamping force possible.

A receiving housing for electronic components and/or a battery can be provided on the ring section on one side. A receiving housing of this type which is arranged asymmetrically on the ring section can be necessary, since it is usually difficult to provide the desired electronic components including the battery solely in a ring section. In particular, the mechanism for guiding the actuating segment can also be integrated more simply if the ring section is supplemented in an asymmetrical way by a receiving housing which is attached to it or integrally formed on it. In particular, a receiving housing of this type is also expedient when the evaluation unit itself is to have a display. A display of this type is usually to be accommodated in the ring section in a scarcely satisfactorily legible manner.

The actuating segment can be movable with respect to the main segment in various ways. Thus, for example, a pivoting movability is conceivable. The actuating segment is preferably guided, however, by way of a sliding guide in a translational manner on the main segment of the evaluation unit. Depending on the configuration, the sliding guide can permit a linear movement or else a movement which takes place in a slight curve.

The sliding guide can be realized in a very simple manner and, in particular on account of the usually linear movability of the actuating button with respect to the base of the discharge head, is suitable to also make an identical movability of the actuating segment with respect to the main segment possible.

The guide section, which, in particular, preferably dips into a housing of the main segment in the case of a sliding guide of this type when the actuating segment is pressed down, is preferably reinforced in order to achieve an increased stability. This can be achieved, in particular, by virtue of the fact that the guide section has a curved cross section. A curved cross section of this type can be provided so as to follow the usually round cross-sectional shape of the actuating button and to surround said actuating button partially.

The actuating segment preferably has a pressing face which protrudes from one side beyond the actuating button, with the result that the actuating button is likewise pressed down indirectly by way of the actuating segment being pressed down.

Said pressing face is that face to which a force is applied directly by the user in the case of an attached evaluation unit, with the result that the risk is low that an actuation of the actuating segment accidentally does not take place in the case of an actuation of the actuating button. The actuating segment preferably protrudes from one side beyond the actuating button, and otherwise leaves the actuating button free at the sides, with the result that the discharge opening remains uninfluenced in the discharge direction despite the protruding actuating button.

The evaluation unit preferably has a transmission device or component, by way of which the movement of the actuating segment with respect to the main segment is converted into a movement which is directed differently or is limited differently, which movement is then utilized for triggering the detection sensor.

The transmission device makes it easier for the force which emanates from the actuating segment to be deflected in such a way that a detection sensor, in particular a switch, which is spaced apart from it is triggered. In particular, the transmission device can carry out a limited movement such that the movement of the actuating button in a first phase brings about the deflection of the transmission device, but then no longer moves the latter further. As a result, the risk is reduced that a detection sensor, for example a switch, is damaged by way of excessive pressing of the actuating segment. For this purpose, in particular, the transmission device can have a contact member which is arranged in such a way that, in the case of movement of the actuating segment, it is first of all likewise moved, and subsequently slides without individual movement on the actuating segment which is moved in a continued manner.

In the case of a set with the second overall design of the evaluation unit, the latter preferably has a sensor unit which comprises the detection sensor. Said sensor unit is arranged between the liquid reservoir of the pump dispenser and the bottom of the receiving container or a closure which is attached on the bottom side.

The arrangement of the detection sensor at the lower second end of the receiving container, possibly in the region of a closure which is provided there, allows a very simple evaluation. In the case of actuation, the sensor unit is pressed together in its entirety. In the case of a mechanically or electronically provided threshold value being reached, an actuation can then be perceived as having taken place by the electronics of the evaluation unit.

In particular, the detection sensor which is arranged in this way can be a force sensor or a pressure sensor which measures the force or the pressure which acts from the liquid reservoir in the direction of the bottom of the receiving container or the closure there.

Two design variants are considered to be particularly advantageous with regard to the second overall design of the evaluation unit.

In the case of a set with the second overall design of the evaluation unit, in the case of a first design variant, the receiving container can have a permanently closed configuration at the second lower end, and, at its first end, can have an opening which is sufficiently great, so that at least the liquid reservoir can be pushed in. "Permanently closed" is also understood to mean a design which, although it fundamentally permits opening, does not permit it with an acceptable effort for the user.

In the case of said design variant, in proper use, the pump dispenser is pushed into the receiving container from above, that is to say from the first end. Here, the receiving container is preferably sufficiently long that at least the liquid reservoir can be received in the receiving container completely or virtually completely (more than 80%).

In order to prevent the pump dispenser, which has been previously pushed into the receiving container, from subsequently falling out of the receiving container, the receiving container is preferably provided with a holding device, by way of which holding device the pump dispenser can be secured in a non-positive or positively locking manner against sliding out. In the simplest case, a holding device of this type can be an elastically deflectable pawl. It is important here that this does not need to be destroyed during the intended removal of the pump dispenser for the purpose of replacement. More complex systems can also provide that the holding device has a part which is separate from the receiving container and, after the pump dispenser has been pushed into the receiving container, is placed on top and is secured, for example, by means of a bayonet or a thread.

In the case of a set with the second overall design of the evaluation unit, in the case of a second design variant, the receiving container can be of an open configuration on both sides, an opening at the first end having an inside cross section which is smaller at least in sections than the maximum cross section of the pump dispenser, with the result that the pump dispenser can be pushed from the inside through the opening only partially, but at least with the discharge opening. In the case of said second design variant, during intended use, the pump dispenser is introduced from the opposite second end, that is to say from below. On account of the size of the opening of the receiving container at the upper first end, the pump dispenser can be pushed in only to a limited extent here.

In the case of said second design variant, it is preferably provided that the evaluation unit has a closure for closing the receiving container at the second end, the closure being configured such that it can be removed and coupled, in order that it can be detached when the old pump dispenser is to be removed or reinserted, and in order that the new pump dispenser can be secured in the receiving container after insertion of said new pump dispenser.

The fastening of the closure to the receiving container can also take place by means of a thread or a bayonet. A frictionally locking coupling is also fundamentally conceivable, but is not preferred.

The closure can be configured as a part which is considerably shorter than the receiving container and merely closes the receiving container at the lower end. The closure can also have a greater length, however, with the result that the fastening of the closure to the receiving container instead takes place centrally between the opposite ends of the evaluation unit.

Together with the receiving container, the closure defines an interior space for the pump dispenser. Said interior space is preferably sufficiently great, in order that at least the liquid reservoir of the pump dispenser can be received therein completely or virtually completely (greater than 80%).

In the case of one design of the evaluation unit with a closure of the described type, it is advantageous if the closure itself has the sensor unit, a plurality of variants being possible here. The closure can directly form the housing for electronic components of the sensor unit. As an alternative, the sensor unit can have a dedicated housing which is provided fixedly or releasably in the closure.

The receiving container is preferably manufactured at least in sections from a transparent material, in particular from a transparent plastic. The transparent design of the receiving container, which allows an inscription on the pump dispenser to be read even after insertion of said pump dispenser into the receiving container, permits precise legibility of the inscription. As a result, different pump dispensers can be identified reliably even when they are inserted in each case into receiving containers of evaluation units.

It is also advantageous in the case of an evaluation unit according to the second design variant if a protective cap is provided. It is fundamentally conceivable that said protective cap is that protective cap which can be fastened to the discharge head of the pump dispenser even in the case of use of the pump dispenser without an evaluation unit. A design of this type limits the construction of the evaluation unit, however, with the result that it is considered to be preferred if the set comprises a protective cap which is configured for releasable fastening to the first end of the receiving container. The dedicated protective cap which is possibly also supplied with the pump dispenser is then no longer used, and is replaced by the protective cap which can be fastened to the receiving container. Said protective cap for fastening to the receiving container can be fastened releasably to the receiving container in a conventional way by means of a coupling with a positively locking or non-positive action.

As has already been mentioned at the outset, the evaluation of the detected data can take place directly at the evaluation unit, with the result that the latter does not need any interfaces, in order to forward the data. One design is preferred, however, in which it is possible for the evaluation unit to transmit detected data to a further device, because this makes deeper analyses and improved visual preparation of the detected data possible.

It is fundamentally conceivable here that the evaluation unit itself is connected to the Internet, for example via WLAN, 4G radio networks or 5G radio networks. It can then transmit the detected data to a central server without a further active device of the user being connected in between.

It is preferred, however, if the set with the pump dispenser and the evaluation unit additionally comprises a mobile evaluation device, in particular in the form of a mobile telephone of the user, which is connected via a wireless interface, in particular the abovementioned Bluetooth interface, to the evaluation unit. Programs for the evaluation of the detected data can run on said mobile evaluation device. Further sensors of the evaluation device can also be used, in order to supplement the data of the evaluation unit. For example, global localization, as is possible, for example, via GPS, is associated with comparatively great technical complexity, with the result that it can be advantageous to keep the evaluation unit free from a corresponding technical design and, instead, to use the mobile evaluation device, that is to say, in particular, a mobile telephone with a program (app), for the detection of the position. It can certainly be expedient, however, to provide the evaluation unit itself with a device for global localization, since it does not always have to be ensured that the mobile evaluation device is at the same location as the evaluation unit.

The data which relate directly to the actuation, such as time and location, can belong to the data which the evaluation unit or the mobile evaluation device stores or evaluates. Characteristic features of the actuation can also be evaluated, however, such as, for example, the actuating speed or the stroke length. The evaluation of ambient parameters, such as, for example, the temperature, can also be expedient. The data are preferably transmitted to a central server either directly by the evaluation unit or by the mobile evaluation device, which central server makes supplementary analyses possible, even across a plurality of users.

The set preferably comprises a mobile evaluation device, in particular in the form of a mobile telephone, which is connected via a wireless interface to the evaluation unit.

BRIEF DESCRIPTION OF THE DRAWINGS

Further advantages and aspects of the invention result from the claims and from the following description of preferred exemplary embodiments of the invention which are described in the following text on the basis of the figures.

DETAILED DESCRIPTION OF THE EXEMPLARY EMBODIMENTS

Figure 1:
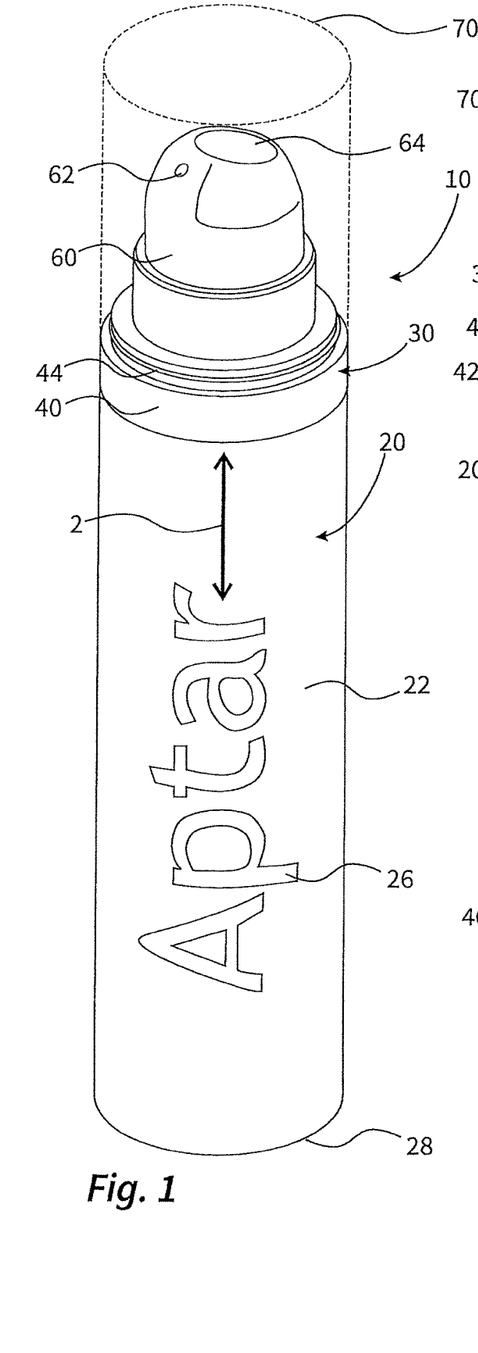
FIG. 1 shows a customary pump dispenser, as known from the prior art.
Figure 2:
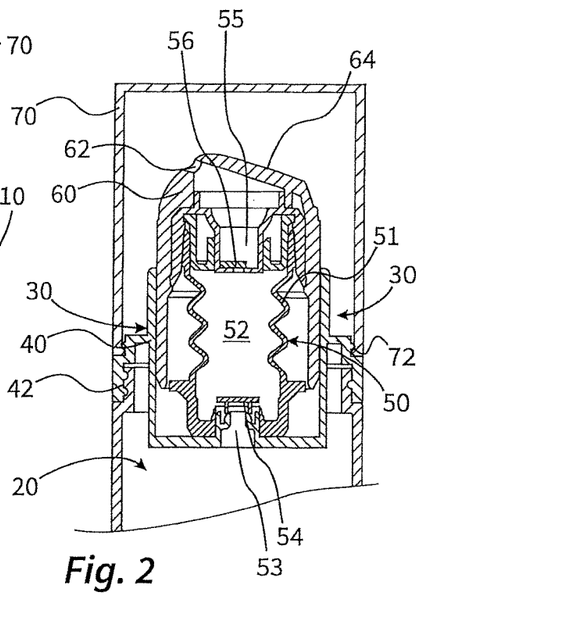
FIGS. 2 and 3 show the method of operation in the case of actuation with respect to the pump dispenser from FIG. 1, in a sectioned illustration.
Figure 3:
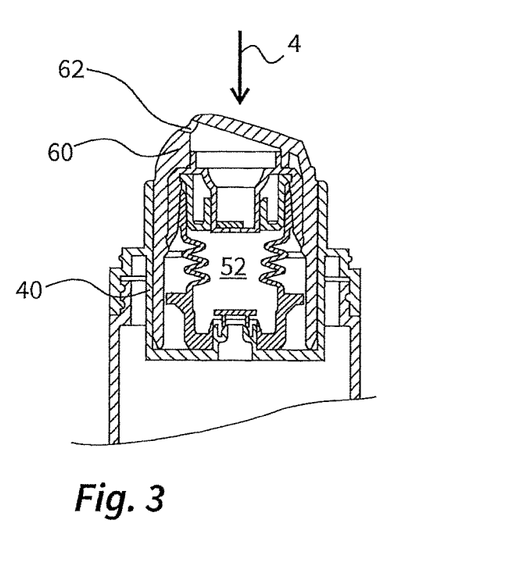

FIGS. 1 to 3 show a substantially conventional pump dispenser, as will be part of a set according to the invention.

With respect to FIG. 1, it can be seen that the pump dispenser 10 has a liquid reservoir 20 which is configured as a container which is open at the top and closed at a bottom 28, on a shell wall 22 of which liquid reservoir 20 an inscription 26 is provided. A discharge head 30 is coupled to the liquid reservoir by means of a coupling device 42 in the manner of a thread. Said discharge head 30 has an actuating button 60 which can be pressed down in the direction of the main direction of extent 2 of the pump dispenser, which actuating button 60, in proper use, is pressed down manually by applying a force in the region of an actuating face 64, in order, as a result, to discharge liquid from the liquid reservoir 20 through a discharge opening 62 which is provided on the actuating button. In the unused state, the discharge head can be covered by way of a protective cap 70 which is fastened to a base 40 of the discharge head in a latching manner in the region of a latching edge 44.

As can be gathered from FIG. 2, a pump device 50 is provided within the discharge head 30. Said pump device 50 comprises a pump chamber 52, the volume of which can be reduced by way of pressing down of the actuating button 60, which pump chamber 52 is connected via an inlet channel 53 to the liquid reservoir 20 and via an outlet channel 55 to the discharge opening 62. Both the inlet channel 53 and the outlet channel 55 in each case have a valve 54, 56. The inlet valve 54 opens in the case of negative pressure in the pump chamber 52 with respect to the liquid reservoir 20 and therefore in the case of an upwardly directed restoring movement of the actuating button 60. In this phase, the outlet valve 56 is closed, since it opens only in the case of positive pressure in the pump chamber 52 with respect to the surrounding atmosphere and otherwise closes. In the case of pressing down of the actuating button 60 in contrast, the outlet valve 56 opens, whereas the inlet valve 54 is closed. In this way, it is possible in the manner which can be seen in FIG. 3 for liquid from the pump chamber 52 to be moved in the actuating direction 4 by way of pressing down of the actuating button 60. In the case of the present exemplary embodiment, the pump device 50 is configured as a bellows pump device, and therefore has a bellows body 51 which surrounds the pump chamber 52. Other possible overall designs are provided, for example, a piston pump, in the case of which, in the case of pressing down of the actuating button 60, a piston is moved within a cylinder in order to reduce the pump chamber 52.

FIGS. 4 to 8 show a first exemplary embodiment of a set according to the invention.

Figures 4, 5:
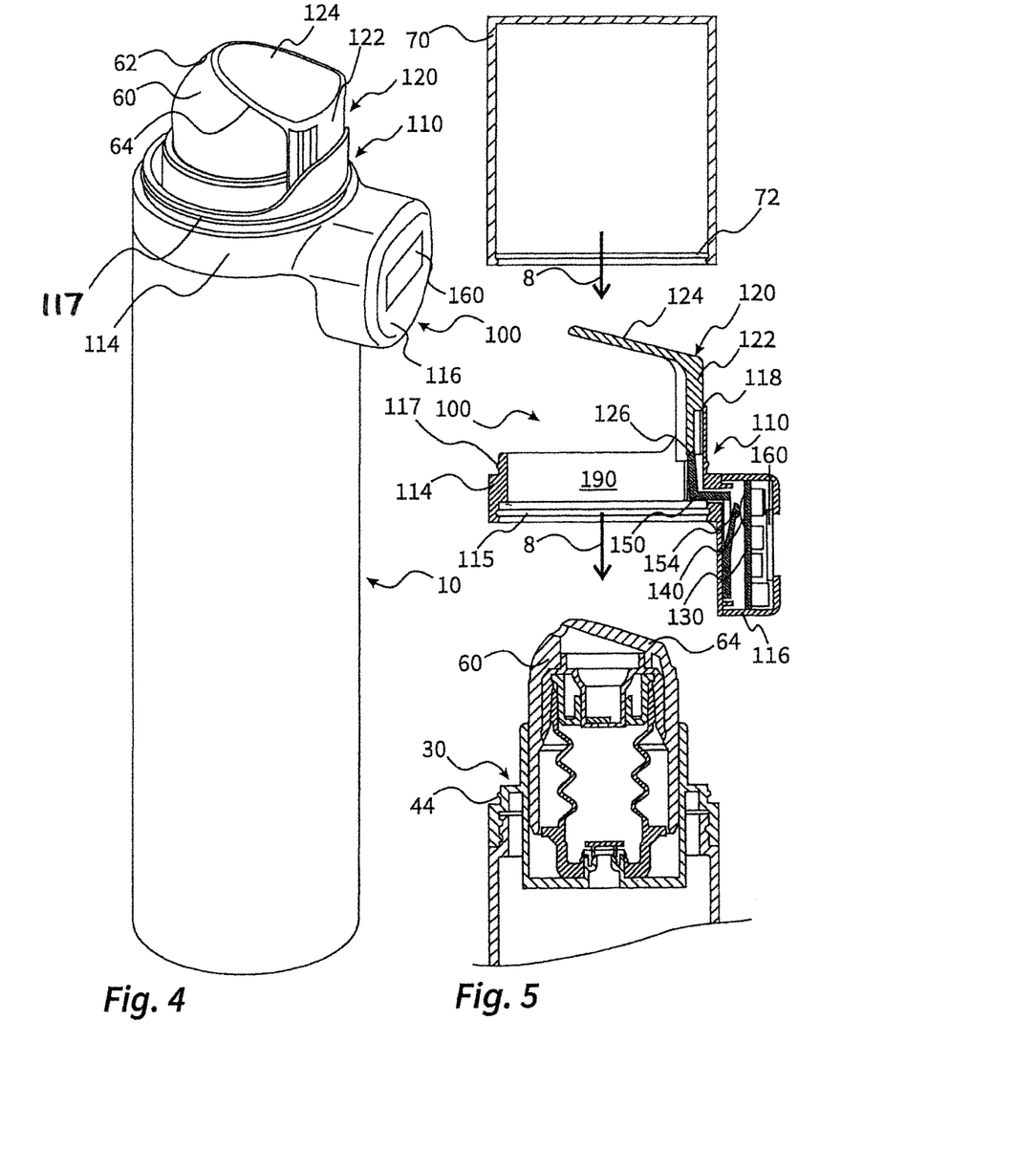
FIG. 4 shows a set according to the invention with the pump dispenser from FIGS. 1 to 3 and an evaluation unit which is attached to the latter in accordance with a first overall design.
FIG. 5 shows a sectioned illustration of the individual components of the set from FIG. 4 and the type of assembly.
Figures 6, 7, 8:
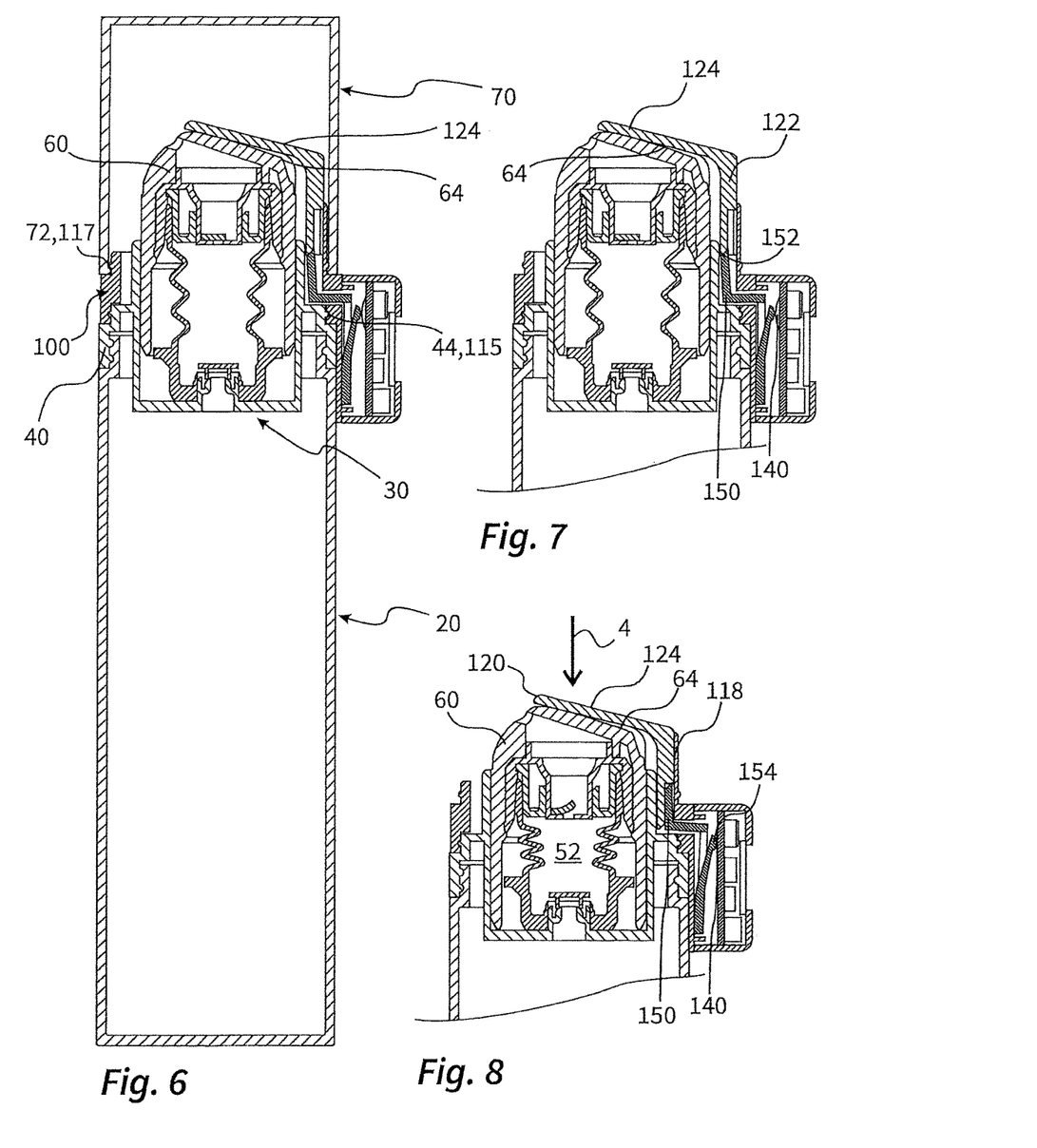
FIG. 6 shows the set according to FIG. 4 in a sectioned illustration after assembly has been concluded.
FIGS. 7 and 8 show the method of operation in the case of actuation with respect to the set from FIG. 4 in a sectioned illustration.

FIG. 4 shows the assembled state, as does FIG. 6. It can be seen that the above-described pump dispenser 10 is supplemented by an evaluation unit 100. Said evaluation unit 100 will be described on the basis of the preassembly situation of FIG. 5, in which it is shown in sectioned form.

The evaluation unit 100 has a ring section 114 which merges on one side into a receiving housing 116 for receiving electronic components. Together, the ring section 114 and the receiving housing 116 form the essential parts of a main segment 110 of the evaluation unit 100. The second element of the evaluation unit 100 which can be seen from the outside is an actuating segment 120 which is provided in an approximately L- shaped form on the upper side of the evaluation unit 100 and can be moved by means of a vertical sliding guide 118 in a translational manner with respect to the main segment 110. This is suitable in a way which will still be explained in the further text for pivoting a transmission device or component 150 which for its part actuates a switch 140.

The switch 140 is part of a sensor unit 130 in the receiving housing 116. Moreover, in a way which is not denoted in greater detail, the sensor unit 130 has radio elements for Bluetooth, WLAN and/or mobile communications (3G, 4G, 5G). Also included, furthermore, are a battery as power supply and further sensors, such as, in particular, a temperature sensor, a GPS chip and an acceleration sensor. In the case of the present exemplary embodiment, furthermore, a display 160 is also provided which can also be dispensed with, however, depending on the intended purpose.

Furthermore, it can be seen with reference to FIG. 5 how the assembly takes place. A coupling device in the manner of a groove 115 is provided on the inner side of the ring section 114 of the main segment 110. Said coupling device is dimensioned in such a way that it can be coupled to the latching edge 44 of the base 40 of the discharge head, this connection or coupling being deliberately very stiff, in order to prevent the evaluation unit from being accidentally pulled off together with the cap. Furthermore, the ring section 114 of the main segment 110 has a latching edge 117 which, with regard to its configuration, corresponds approximately to that of the latching edge 44, with the result that the protective cap 70 can be latched here with a latching groove 72 which is provided on the cap 70. Arrow 8 represents the assembly direction for the cap 70 and the evaluation unit 100.

In other words, in the case of the assembly of a set according to FIGS. 4 to 8, the evaluation unit 100 is fastened to the discharge head 30 where otherwise the protective cap 70 would be fastened. The protective cap 70 for its part is fastened to the latching edge 117 of the evaluation unit 100.

FIG. 6 shows a sectioned illustration of the assembled state.

The operation is clarified on the basis of FIGS. 7 and 8. The actuating segment 120 of the evaluation unit 100 protrudes beyond the actuating face 64 of the actuating button with the result that an application of a force to the actuating button 60 takes place in a manner which is intuitive and obvious to the user by way of pressing down of the actuating segment 120. For this purpose, a pressing face 124 is provided on the upper side of the actuating segment 120. If the actuating segment 120 is pressed down in the actuating direction 4 in the way shown in FIG. 8, this also leads to pressing down of the actuating button 60 and, accordingly, to a discharge of liquid.

At the same time, however, a lower edge 152 provided on a vertical part 122 of the actuating segment 120 presses the transmission component 150 to the side, as FIG. 8 shows. Said transmission component 150 pivots in the process about a pivot axis which is provided at the lower end of the transmission component 150, with the result that a boom 154 triggers the switch 140 and therefore allows said sensor unit 130 of the evaluation unit 100 to detect the discharge operation which has taken place. The sensor module can store the actuation together with time stamp, location specification and/or data of the other sensors, and/or can transmit it in a wireless manner to a receiver.

Continued pressing down of the actuating segment 120 does not lead to a further deflection of the transmission component 150, since the latter slides along on the actuating segment 120. There is therefore no reason to fear that an excessively great movement of the actuating segment 120 damages any other components of the evaluation unit 100.

FIGS. 9 to 12 show a second exemplary embodiment. A pump dispenser 10 is also used here, which pump dispenser 10 can be configured in the same way as that shown in FIGS. 1 to 3.

In addition, a set according to FIGS. 9 to 12 comprises an evaluation unit 200 which is formed in this case primarily as a receiving container 210, on the lower bottom 214 of which a sensor unit 230 rests. A force or pressure sensor 242 is arranged in said sensor unit 230, which force or pressure sensor 242 can be triggered by way of force applied to the upper side 232 of the sensor unit 230. The receiving container 210 has a length, in which the pump dispenser 10 can be received predominantly and its liquid reservoir 20 can be received completely.

Figures 11, 12:
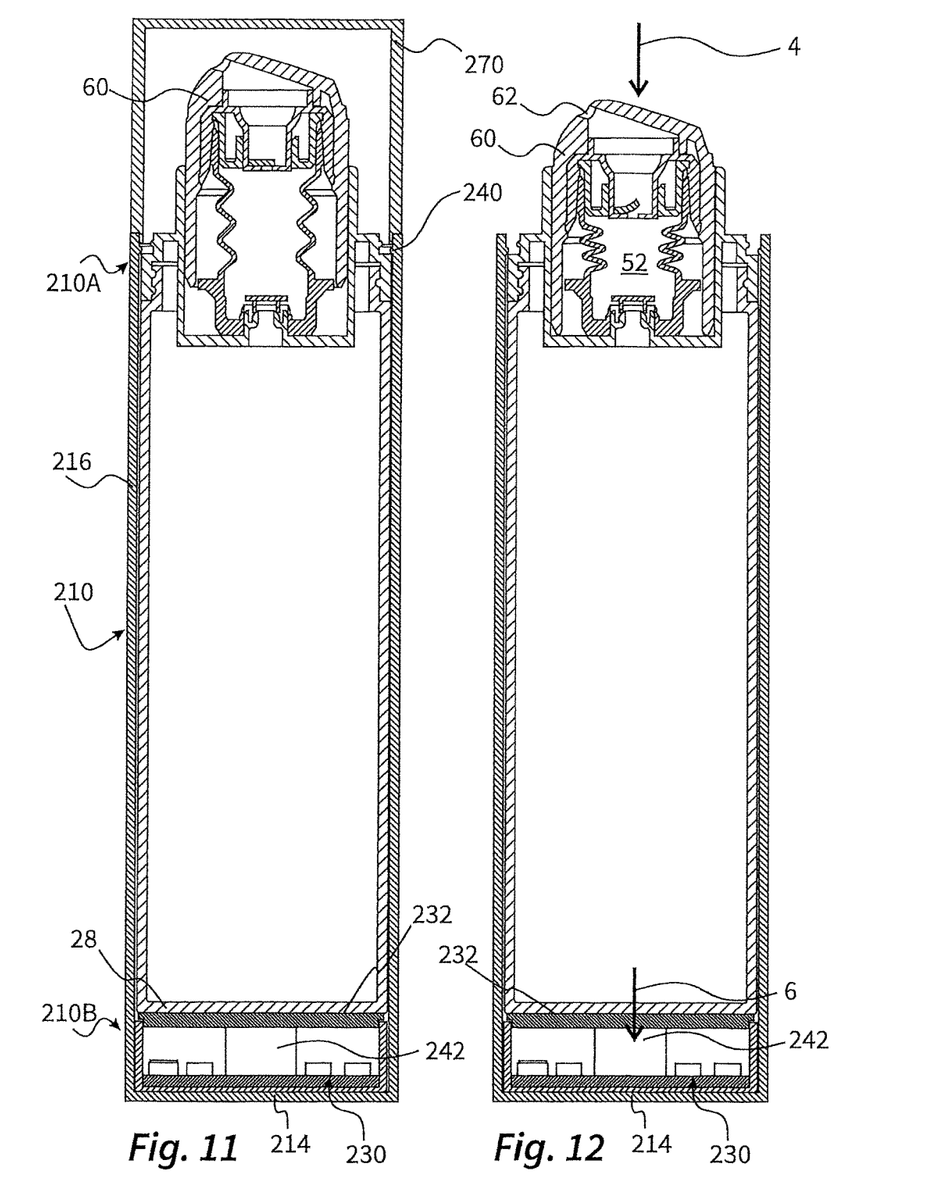
FIG. 12 shows the method of operation in the case of actuation with respect to the set from FIG. 9 in a sectioned illustration.

FIG. 11 shows the assembled state. It can be seen that a holding device 240 in the form of a latching ring on the inner side of the receiving container 210 at its upper end 210A ensures that the inserted pump dispenser 10 is not at risk of slipping out of the receiving container 210. Furthermore, it can be seen that the liquid reservoir 20 of the pump dispenser 10 lies with its bottom 28 on the upper side 232 of the sensor unit 230. FIG. 11 shows, furthermore, that the set has a protective cap 270 which, in the present case, is fastened via a frictionally locking coupling to the upper end 210A of the receiving container 210.

Figure 9:
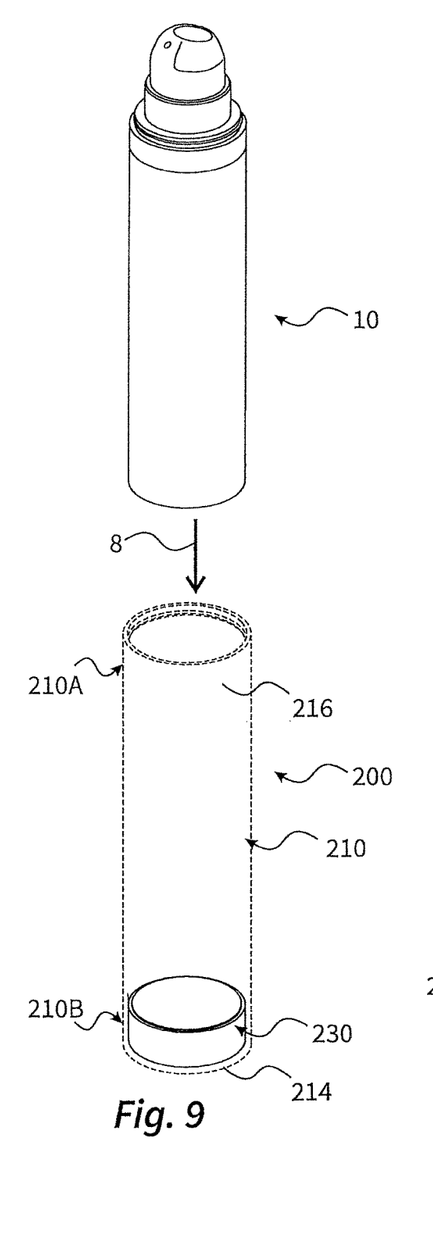
FIG. 9 shows a set according to the invention with the pump dispenser from FIGS. 1 to 3 and an evaluation unit which is attached to the latter in accordance with a second overall design in a first design variant.
Figure 10:
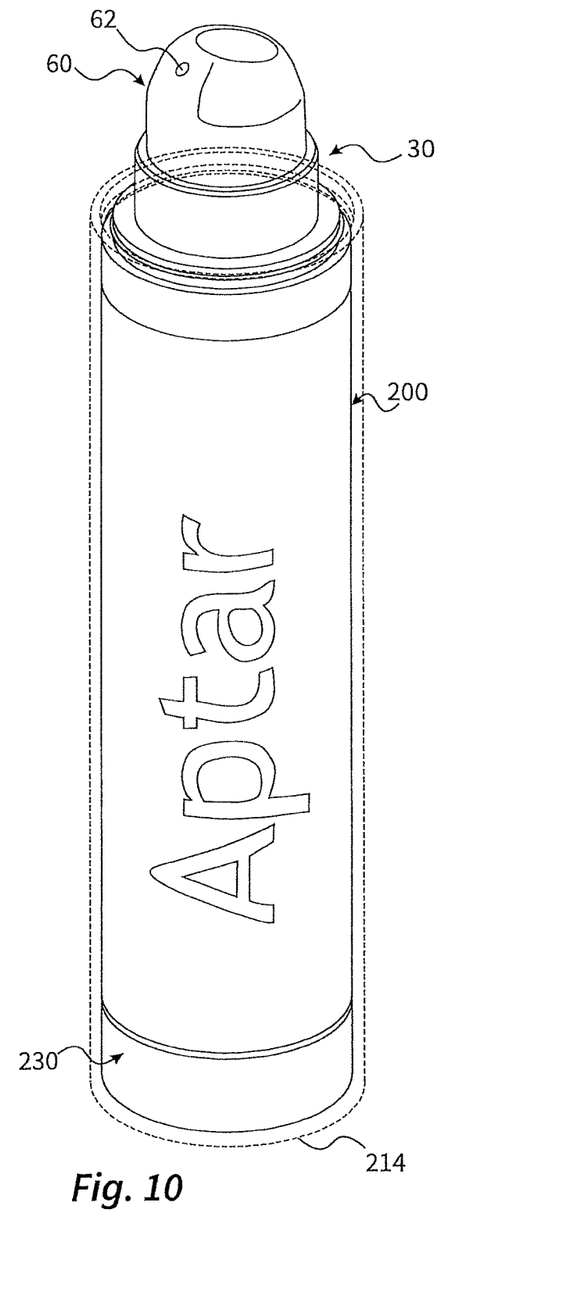
FIGS. 10 and 11 show the set from FIG. 9 after assembly has been concluded.

FIG. 12 clarifies the use of the set according to FIGS. 9 to 11. During said use, a user usually grips around the receiving container 210 at least with his/her thumb and middle finger, and actuates the actuating button 60 in the actuating direction 4 by means of his/her index finger. In the way which has already been described above, the force which is applied here brings about the reduction in volume of the pump chamber 52 and therefore the discharge of liquid from the pump chamber 52.

Furthermore, said force also acts (indicated by way of the arrow 6) on the upper side 232 of the sensor unit 230, however, and therefore makes it possible for the electronic components of the evaluation unit 200 to detect the discharge operation. Proceeding from the detected actuation, the further processing can take place in the above-described manner.

FIGS. 13 to 16 show a design of similar type. Here too, a pump dispenser 10 in accordance with that from FIGS. 1 to 3 is provided, which pump dispenser 10 is received in a receiving container 210.

Figure 13:
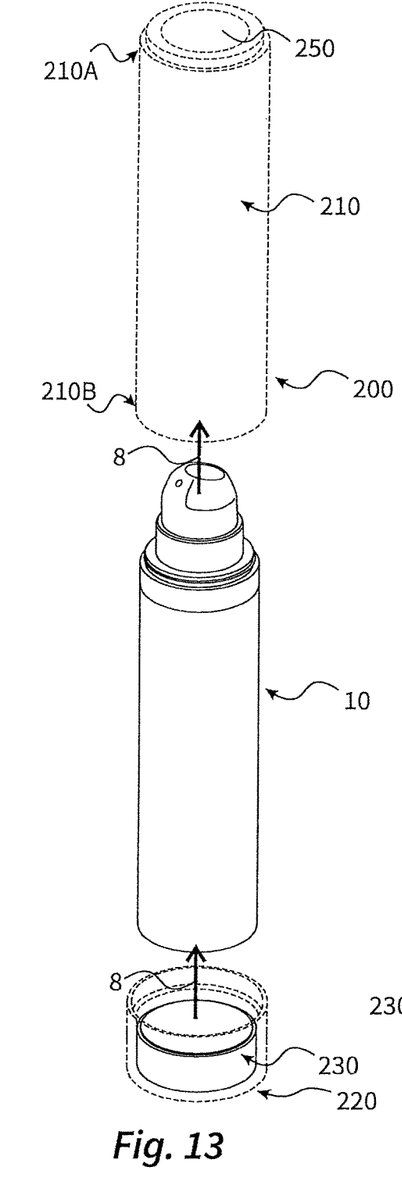
FIG. 13 shows a set according to the invention with the pump dispenser from FIGS. 1 to 3 and an evaluation unit which is attached to the latter in accordance with a second overall design in a second design variant.
Figure 14:
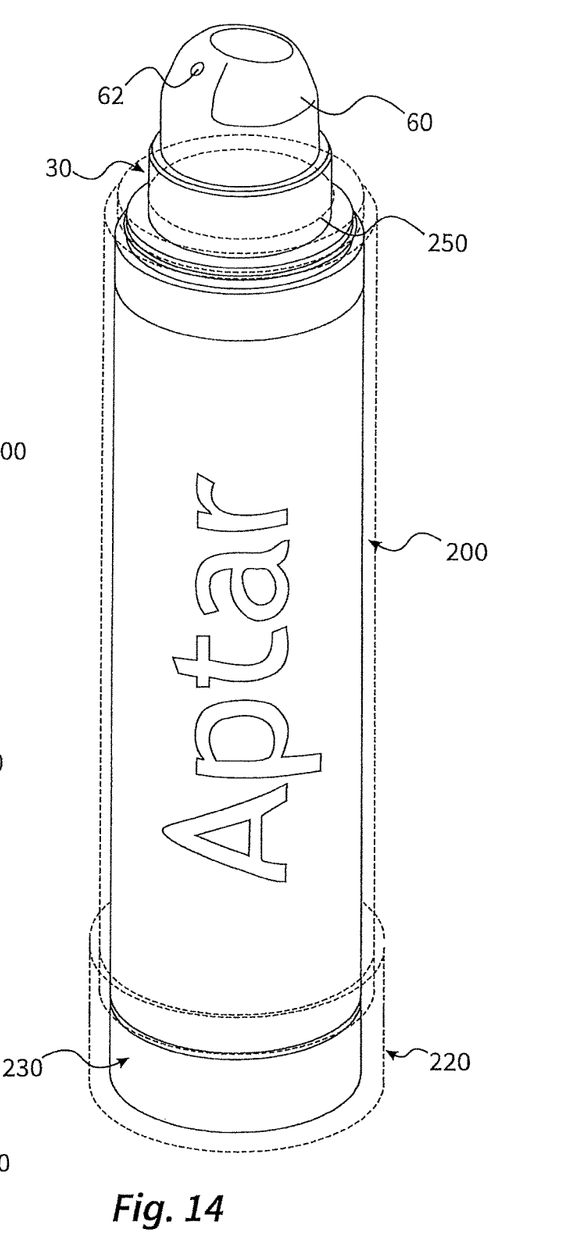
FIGS. 14 and 15 show the set from FIG. 13 after assembly has been concluded.
Figures 15, 16:
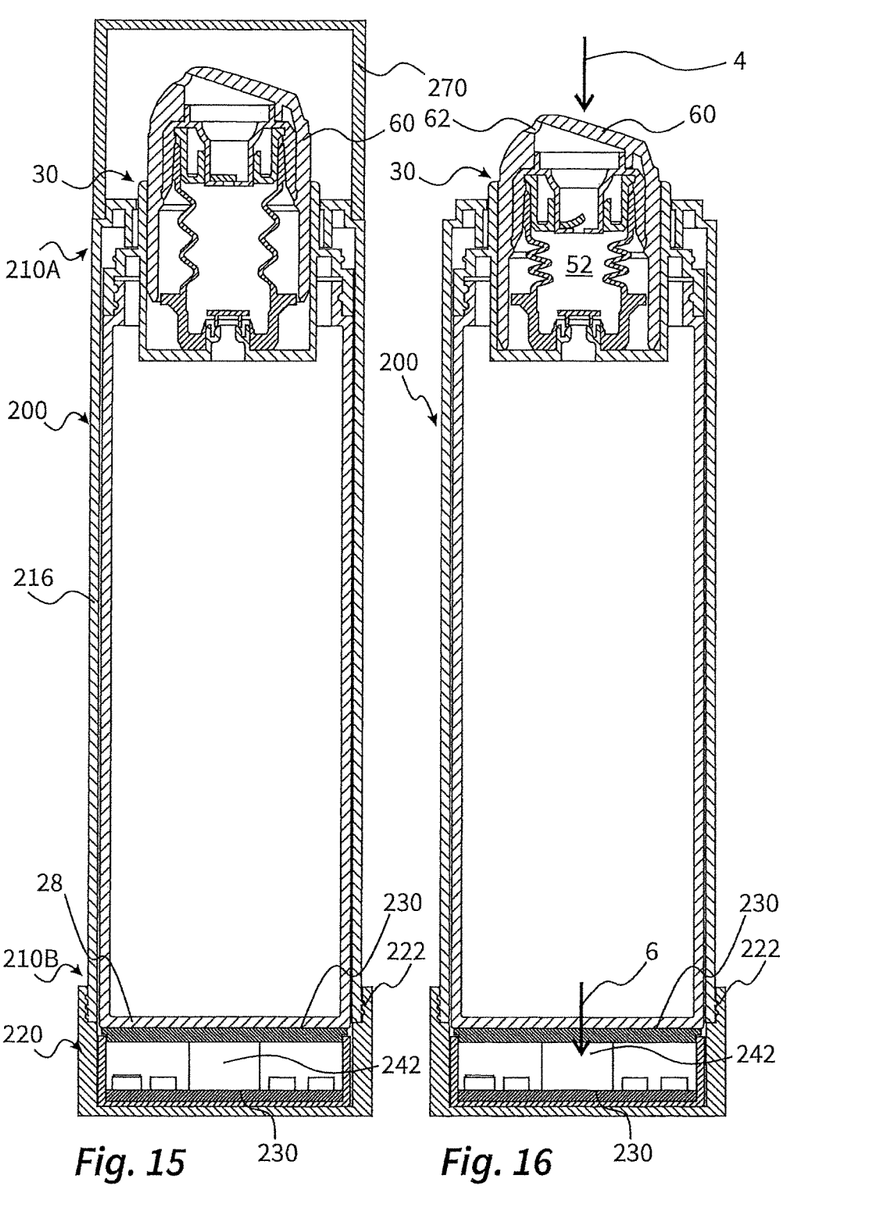
FIG. 16 shows the method of operation in the case of actuation with respect to the set from FIG. 13 in a sectioned illustration.

In this case, however, the pump dispenser 10 is pushed from below in the assembly direction into the receiving container 210, with the result that ultimately the discharge head 30 or at least the actuating button 60 protrudes out of an opening 250 of the receiving container 210 at the top. A closure 220 is fastened in the assembly direction 8 by means of a thread 222 to the lower end 210B of the receiving container, said closure having a sensor unit 230 which is similar or identical to that of the preceding exemplary embodiment.

The fundamental method of operation (shown in FIGS. 15 and 16) is the same as that in FIGS. 11 and 12. Here too, the actuation acts in the actuating direction 4 on the sensor unit 230, with the result that the force or pressure sensor 242 triggers and makes further processing of said information possible in the above-described way.

A substantial difference arises only in the case of the replacement of the pump dispenser. In the case of the design according to FIGS. 13 to 16, the closure 220 is first of all to be unscrewed for the purpose of the replacement, and the pump dispenser 10 is then to be removed and replaced by a new pump dispenser 10, with the result that the closure 220 can then be screwed on again.

The described receiving containers 210 are manufactured from a transparent plastic, with the result that the inscription 26 remains legible despite the presence of the receiving container.

Figure 17:
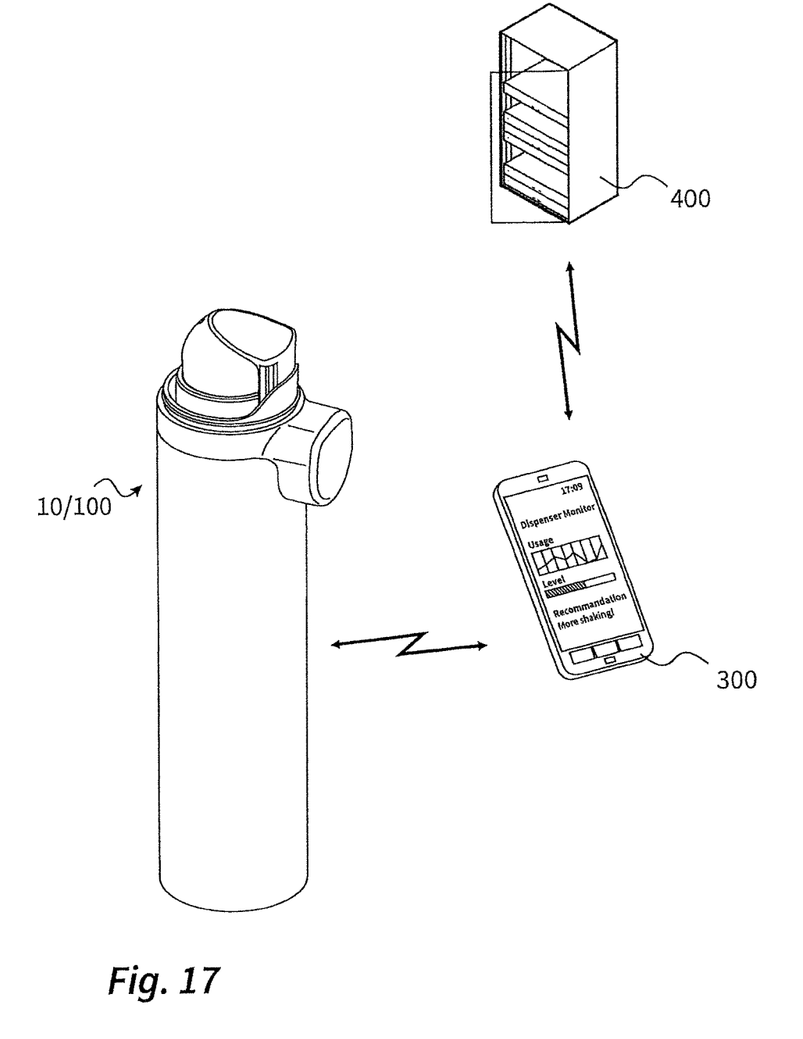
FIG. 17 shows the connection of a set according to the invention by way of a mobile telephone to a central server.

FIG. 17 shows (by way of example on the basis of the set according to FIGS. 4 to 8) the method of operation of the set with regard to the data transfer. In its receiving housing 116, the pump dispenser 10 which is provided with the evaluation unit 100 has a wireless interface in accordance with the Bluetooth standard. Via this, the evaluation unit 100 is coupled to a separate evaluation device 300, in the present case in the manner of a mobile telephone. This means that, in the case of every discharge which has taken place or at a later time in the case of an absence of the evaluation device, the evaluation unit 100 transmits the actuation to the mobile evaluation device 300, where the data can be aggregated and evaluated.

The data can also be supplemented with further data. Thus, for example, the GPS chip set of the mobile telephone can be used, in order to supplement the data with the location of the actuation.

The mobile evaluation device 300 is connected via the Internet to a central server 400 which can be located, in particular, in the area of control of the manufacturer of the pump dispenser. As a result, said manufacturer receives data about the usage which it can use for improvement of the product. After evaluation of the data from the mobile evaluation device 300, the central server 400 can also send the latter information with respect to suggested actions for the user. It is also conceivable that the filling level of the dispenser is taken into consideration and an additional delivery of a pump dispenser is possibly offered or takes place automatically.

The determination of the filling level of the pump dispenser is firstly possible indirectly via the fact that the number of discharge operations is counted. It is also conceivable, however, that, for example, the sensor unit 230 is capable of determining how much liquid still remains in the pump dispenser 10 on the basis of the weight of said pump dispenser which weight acts on said sensor unit 230 in the rest state.

The invention claimed is:

1. A dispenser set for discharging pharmaceutical or cosmetic liquids, the dispenser set comprising:
a pump dispenser and an evaluation unit, the pump dispenser comprising:
 a liquid reservoir having an upper end;
 a discharge head attached to the upper end of the liquid reservoir, the discharge head comprising:
  a discharge opening;
  a base fastened to the liquid reservoir;
  an actuating button pressable downwardly with respect to the base to discharge liquid from the liquid reservoir; and
  a pump device actuated by pressing the actuating button downwardly, the pump device, when actuated, conveying liquid from an inlet channel connected to the liquid reservoir to the discharge opening;
the evaluation unit being configured for detecting actuation of the pump device, the evaluation unit being configured as an external evaluation unit and comprising:
 a main segment releasably attached in a stationary manner to the liquid reservoir or the base of the discharge head;
 an actuating segment having a pressing face, the pressing face being disposed and configured to permit manual movement of the actuating segment with respect to the main segment, the actuating segment being disposed on or above the actuating button such that, when the pressing face of the actuating segment is manually pressed down with respect to the base, the actuating button is pressed down indirectly; and
 a detection sensor, the detection sensor detecting movement of the actuating segment with respect to the main segment.

2. The dispenser set as claimed in claim 1, further comprising a protective cap, the protective cap in a fitted state covering the actuating button and/or the discharge opening.

3. The dispenser set as claimed in claim 2, wherein the protective cap is releasably couplable to the discharge head and the main segment.

4. The dispenser set as claimed in claim 2, wherein the protective cap is configured for a latching coupling on the main segment of the evaluation unit, and the main segment is configured for a latching coupling on the discharge head.

5. The dispenser set as claimed in claim 1, wherein the main segment of the evaluation unit has a free region and a ring section surrounding the free region, the pump dispenser being pushed through the free region into a coupling position.

6. The dispenser set as claimed in claim 5, wherein the evaluation unit further comprises a receiving housing for electronic components and/or a battery, the receiving housing being disposed on a side of the ring section.

7. The dispenser set as claimed in claim 1, further comprising a sliding guide configured to guide the actuating segment in a translational manner on the main segment of the evaluation unit.

8. The dispenser set as claimed in claim 7, wherein the actuating segment has a guide section cooperating with the sliding guide, the guide section having a curved cross-section configured to partially surround the actuating button.

9. The dispenser set as claimed in claim 1, wherein the evaluation unit has a transmission device, the transmission device converting movement of the actuating segment with respect to the main segment into a movement for triggering the detection sensor.

10. The dispenser set as claimed in claim 9, wherein the transmission device has a contact member arranged such that movement of the actuating segment first causes movement of the contact member, and the contact member subsequently, during continued movement of the actuating segment, slides relative to the actuating segment.

11. The dispenser set as claimed in claim 1, wherein:
the liquid reservoir of the pump dispenser is connected via a snap-action connection or a threaded connection to the discharge head; and/or
the liquid reservoir is shaped in a substantially cylindrical manner; and/or
the liquid reservoir has an outer side provided with an inscription; and/or
the pump device has a pump chamber, an inlet-side inlet valve and an outlet-side outlet valve, the inlet valve opening in case of a negative pressure in the pump chamber with respect to the liquid reservoir, and the outlet valve opening in case of a positive pressure in the pump chamber with respect to the surrounding atmosphere; and/or
the discharge opening is provided on the actuating button such that, when the actuating button is pressed downwardly with respect to the base of the discharge head, the discharge opening is likewise pressed down; and/or
the liquid reservoir is filled with a cosmetic or pharmaceutical liquid.

12. The dispenser set as claimed in claim 1, further comprising a mobile evaluation device connected via a wireless interface to the evaluation unit.

13. The dispenser set as claimed in claim 12, wherein the mobile evaluation device comprises a mobile telephone.

14. The dispenser set as claimed in claim 12, wherein the wireless interface comprises a Bluetooth interface.

15. The dispenser set as claimed in claim 12, wherein the evaluation unit has a memory, the memory storing data detected by the detection sensor such that when there is a radio connection, the data is transmitted to the mobile evaluation device or to a central server.

16. The dispenser set as claimed in claim 1, wherein the detection sensor comprises a displacement sensor.

17. The dispenser set as claimed in claim 16, wherein the displacement sensor comprises a switch.

18. The dispenser set as claimed in claim 1, wherein:
the evaluation unit has at least one acceleration sensor; and/or
the evaluation unit has at least one sensor comprising a global position detection device; and/or
the evaluation unit is configured, upon each actuation detected by the detection sensor, to store time, location, characteristic features of the actuation or surrounding parameters, and/or to communicate via the Internet to a central server; and/or
the evaluation unit has an indicator device comprising light emitting diodes or a display.

19. The dispenser set as claimed in claim 1, wherein the pressing face of the actuating segment is disposed above and adjacent to the actuating button and faces away from the actuating button.

20. A set for discharging pharmaceutical or cosmetic liquids, said set comprising:
a pump dispenser, said pump dispenser comprising:
a liquid reservoir having an upper end region; and
a discharge head, said discharge head comprising:
a discharge opening;
a base connected to said upper end region of said liquid reservoir;
an actuating button pressable downwardly with respect to said base to discharge liquid from said liquid reservoir; and
a pump device operatively connected to said actuating button such that said pump device is actuated when said actuating button is pressed downwardly to convey liquid from said liquid reservoir to said discharge opening;
said set further comprising an evaluation unit for detecting actuation of said pump device, said evaluation unit comprising:
a main segment configured for releasable attachment to said upper end region of said liquid reservoir or said base of said discharge head;
an actuating segment movable relative to said main segment and disposed above and adjacent to said actuating button, said actuating segment having an actuating face disposed to face away from said actuating button and to receive a manual and downwardly-directed pressing force applied by a user, wherein when a manual and downwardly- directed pressing force is applied to said actuating face said actuating segment displaces said actuating button downwardly; and
a detection sensor, said detection sensor detecting movement of said actuating segment with respect to said main segment.

* * * * *